United States Patent [19]

Davies

[11] Patent Number: 5,294,794
[45] Date of Patent: Mar. 15, 1994

[54] AUTOMATIC COMPENSATION FOR ION MOBILITY SENSOR

[75] Inventor: David K. Davies, Churchill Borough, Pa.

[73] Assignee: Thermo King Corporation, Minneapolis, Minn.

[21] Appl. No.: 18,974

[22] Filed: Feb. 18, 1993

[51] Int. Cl.⁵ .............................................. H01V 49/40
[52] U.S. Cl. ..................................... 250/287; 250/282
[58] Field of Search ........................ 250/287, 286, 282

[56] References Cited

U.S. PATENT DOCUMENTS

| | | |
|---|---|---|
| 3,593,018 | 7/1971 | Cohen . |
| 3,621,239 | 11/1971 | Cohen . |
| 3,624,389 | 11/1971 | Cohen et al. . |
| 3,626,178 | 12/1971 | Cohen . |
| 3,626,181 | 12/1971 | Wernlund . |
| 3,626,182 | 12/1971 | Cohen . |
| 3,629,574 | 12/1971 | Carroll . |
| 3,639,757 | 2/1972 | Caroll et al. . |
| 3,699,333 | 10/1972 | Cohen et al. . |
| 3,812,355 | 5/1974 | Wernlund et al. . |
| 4,259,573 | 3/1981 | Prober et al. . |
| 4,445,038 | 4/1984 | Spangler et al. . |
| 4,551,624 | 11/1985 | Spangler et al. . |
| 4,777,363 | 10/1988 | Eiceman et al. . |

*Primary Examiner*—Jack I. Berman
*Attorney, Agent, or Firm*—M. J. Moran

[57] ABSTRACT

A system for compensating for changes in pressure and temperature in an ion mobility sensor has first and second electrodes positioned a selected distance apart, with a unidirectional electric drift field provided between the electrodes. An ionization source generates ions in the sensor and a trigger controller allows ions to enter the region between the first and second electrodes at a time $t_1$. A time $t_2$ at which a selected ion species travels to one of the first and second electrodes is measured and a time to amplitude converter generates a voltage signal proportional to the difference between $t_1$ and $t_2$, representing the actual travel time of the ion species. A feedback control circuit adjusts the drift field and either the voltage pulse (in pulsed ionization) or the shutter voltage (in continuous ionization) by an amount proportional to the difference between the actual travel time voltage and a voltage proportional to a reference travel time of the selected ion species at a known pressure and temperature.

20 Claims, 6 Drawing Sheets

AUTOMATIC COMPENSATION FOR ION MOBILITY SENSOR

BACKGROUND OF THE INVENTION

1. Field of the Invention

This invention relates generally to devices for quantitatively measuring the concentrations of constituents of multicomponent gaseous samples, and more particularly to devices that conduct such measurements based upon the mobility of ions in drift region.

2. Description of the Prior Art

Ion mobility spectroscopy is a powerful and well known method for providing quantitative measurements of the composition of a gaseous environment. In this context, the ion mobility sensor is usually designed for operation at atmospheric pressure although in principle it can operate at higher or lower pressures. The ion mobility sensor typically is comprised of two identifiable regions: (i) an ionization region where ions are formed representative of the gas sample to be analyzed, and (ii) a drift region into which the ions are injected and allowed to drift in an electric field before collection.

During the ions, drift in the drift region, the ions make many collisions with the sample gas and their motion in the electric field is characterized by the ion mobility. Since the ion mobility is a function of ion mass, ions of different mass segregate during their drift. Thus, by measuring the ion arrival time spectrum at the collector, a signature of the gas sample composition is obtained. Although positive ion spectra provide a selective signature for all gaseous species, the additional monitoring of negative ion spectra (for electronegative species) can provide supplementary information for either diagnostic or calibration purposes.

In currently available commercial instruments, the dimensions of the ionization region are comparable in magnitude to those of the drift region. The ions are produced primarily through ion-molecule reactions, where the impurity molecules of interest are ionized as a result of collisions with primary ions not necessarily derived from the background sample gas but rather from carrier gases deliberately introduced into the reaction region. These primary ions are produced as a result of collisions of beta particles emitted from a Ni-63 radioactive source (located within the ionization region) interacting with the sample and/or carrier gas. Since the beta particles are produced continuously, the ion production process is continuous and the species present in the ionization region represent an equilibrium composition developed over a relatively long time and which includes (deliberately in the case of the use of a carrier gas) ions produced as a result of ion molecule chemistry. Thus, in order to analyze the ions present in this equilibrium ion "sea", provision must be made to extract a pulse of ions into the drift region. This is usually accomplished using an electronic shutter whereby ions are only allowed into the drift region during the application of suitable electric potentials to the shutter electrodes. The detection limit of commercially available sensors depends on the particular species, and levels below one part per billion have been detected for certain organic molecules in air samples at atmospheric pressure without any preconcentration.

Although the ion mobility spectrometer is a well proven instrument, presently available models are relatively large, expensive and require ancillary gas supplies for calibration and for enhancing the ionization efficiency. In addition, present ion mobility spectrometers utilize a continuous nonadjustable ionization energy source. The ionization energy source is typically radioactive which is frequently undesirable. Because a continuous source has been presently used, a shutter is needed to inject a pulse of the total ions into the drift region. The shutter is typically a grid electrode that has a shutter voltage applied to it that injects the ions into the drift region.

The continuous source of the ionization energy is fixed and cannot be changed. Thus, when a complex molecule is being ionized, more than one species of ion may be generated if it interacts with sufficiently energetic electrons. This will disassociate the molecule into smaller fragments and some of those smaller fragments will also be ionized and so on. Therefore, there is very little control over which species of ion can be generated in current ionization methods.

In ion mobility spectrometers, the selectivity of the sensor is derived from the dependence of the ion mobility on ion mass. Thus, the transit time $t_k$ of ions of a particular species k is given by $t_k = d_d/w_k$, where $d_d$ is the ion drift distance and $w_k$ is the ion drift velocity. The drift velocity is a function of $E_d/N$, the ratio of the drift electric field to total gas density. Since the density of a noncompressible gas is related to the pressure p and absolute temperature T through the relation $N = P/(KT)$, where K is Boltzmann's constant, it follows that changes in sample pressure, temperature, or both result in changes in the gas density N. If the field $E_d$ is fixed, then changes in N also lead to changes in $E_d/N$ and thereby $w_k$. Thus, the expected arrival time $t_k$ of ions of species k changes with pressure or temperature. In order to provide calibrated time signatures at the collector, the sample pressure and temperature are usually monitored using separate sensors so that appropriate compensation can be applied to the collected raw data. The necessity for two additional sensors increases the hardware complexity and introduces further potential reliability concerns.

It would also be advantageous to provide ion mobility sensors with a means for triggering an alarm when the concentration of a monitored species rises above some preset value. Alternatively, it would be advantageous to provide a means for the measuring of one or more different species.

SUMMARY OF THE INVENTION

I provide an ion mobility sensor having an ionization region and an ion drift region. The ionization region is preferably bounded by a grid cathode and an anode. It is into this ionization region that the gaseous sample enters, either by an opening to ambient in an open system or by a feed pipe in a closed system. In the context of positive ion sampling, the ion drift region is bounded by the grid cathode and a by a guarded ion collector. The ion collector consists of an electrode and its associated shield. Application of suitable potentials to this electrode arrangement establishes nominally uniform electric fields $E_i$ and $E_d$ in the ionization and drift regions respectively.

DC voltages applied to the anode, cathode and collector electrodes establish a unidirectional DC field across the entire sensor. A superimposed voltage pulse is provided at the anode which results in a field $E_i$ in the ionization region which is higher than the DC breakdown field but of sufficiently low amplitude and duration to avoid the development of an arc in the ionization region.

During the application of the voltage pulse, a pulse of ultraviolet (UV) radiation from a flash tube or other UV source irradiates the cathode grid, liberating a pulse of photo electrons from the cathode grid. Preferably, the anode is of a type that is semi-transparent to UV light, such as a grid anode or a semi-transparent conducting film anode. When the anode is semi-transparent, the UV light may be irradiated through the anode towards the cathode. The UV pulse liberates a pulse of photoelectrons from the cathode which in the presence of the pulsed high electric field generates a pulsed non-equilibrium discharge between the cathode and anode. The pulsed non-equilibrium discharge results from avalanching of the initial photoelectrons in ionizing collisions with the sample gas during the drift of the electrons to the anode, and gives rise to a pulse of ions characteristic of the sample gas in the volume between cathode and anode. The non-equilibrium discharge is characterized as that in which the mean energy of the electrons is considerably larger than that of the ions or neutral molecules. The avalanche growth of current is due to primary ionizing collisions between electrons and the sample gas during their drift to the anode as well as by secondary ionizing collisions between excited or ionized air molecules and the minority species. The minority species, in the case of large organic molecules, have relatively low ionization thresholds.

The positive ion pulse formed drifts toward the cathode grid and a fraction of the ions pass through the grid into the drift field region. After drifting across the drift region, these positive ions are collected by the ion collector. Because this collector is shielded from the drift region by a screened guard that is held at a potential consistent with the local electric field, the ions are only detected at the collector after they pass through the guard, and displacement current due to the motion of all ion species between the cathode and the shield is not observed by the detection circuit.

In general, the drift time of the different ion species is dependent on the charge and mass of the particular ions produced in the ionization region so that the detected ion signal comprises a series of pulses, each corresponding to a different species. Thus, provided that the mobilities of the different ions are known, the detector signal provides a signature of the different species present in the gaseous sample.

Although the electrodes of the preferred ion mobility sensor are configured to collect positive ions, it is understood that the polarity of the electrodes could be reversed for the collection of negative ions.

Once the ion pulses are received at the collector electrode as an electrical charge, the ion pulses are processed to evaluate the characteristics of the sample. The circuitry that processes the ion pulses is controlled by a trigger control. The trigger control also controls the timing of the UV pulse source and the pulsed voltage source such that the processing of electrical data representing the ion pulses will coincide with the receiving of that data from the collector electrode.

The first preferred implementation of the ion mobility sensor senses one or more optionally variable, predetermined species in a specific gaseous sample. In the first implementation, an alarm is triggered if the concentration of the monitored species in the sample rises above some preset value. This value may be variable and may be different for the different species monitored.

The second preferred implementation of the ion mobility sensor involves integration of the sensor into a quantitative microprocessor-based system for the comprehensive measurement of one or more different selectable species.

Practical implementations for ion mobility sensors are also provided. The implementations involve triggering an alarm or other signaling means when the concentration of a monitored species rises above some preset value or, alternatively, measuring one or more selected species in a gaseous sample. A trigger control is employed for controlling the timing of ion pulse creation in the sensor. The trigger control also controls the operation of the circuitry for evaluating the received ion pulses.

We also provide automatic compensation means which enables the operating pressure and temperature to be compensated for in an ion mobility sensor. In the case of a conventional ion mobility sensor, this compensation automatically calibrates the time scale so that the arrival time of ions at a given species is invarient to changes in the pressure and temperature of the sample gas. In the case of the preferred ion mobility sensor disclosed herein, the automatic compensation means also automatically compensates the sensitivity of the ion mobility sensor for changes in pressure and temperature.

The sensor may be applied to detect a wide range of substances in many different environments, such as the presence of chemical and/or biological agents including impurities in refrigerant systems for the protection of compressors and other components, and refrigerated environments for optimizing cargo protection. The sensor may also be used to detect the presence of illegal drugs and explosives in containers and on personnel. Toxic storage, workplace or waste areas may be monitored as may areas for the presence of vapor fuels or other explosives. Anesthesia procedures may also be monitored.

Other details, objects and advantages of the invention will become apparent as the following description of certain present preferred embodiments thereof proceeds.

DETAILED DESCRIPTION OF THE PREFERRED EMBODIMENT

Figure 1:
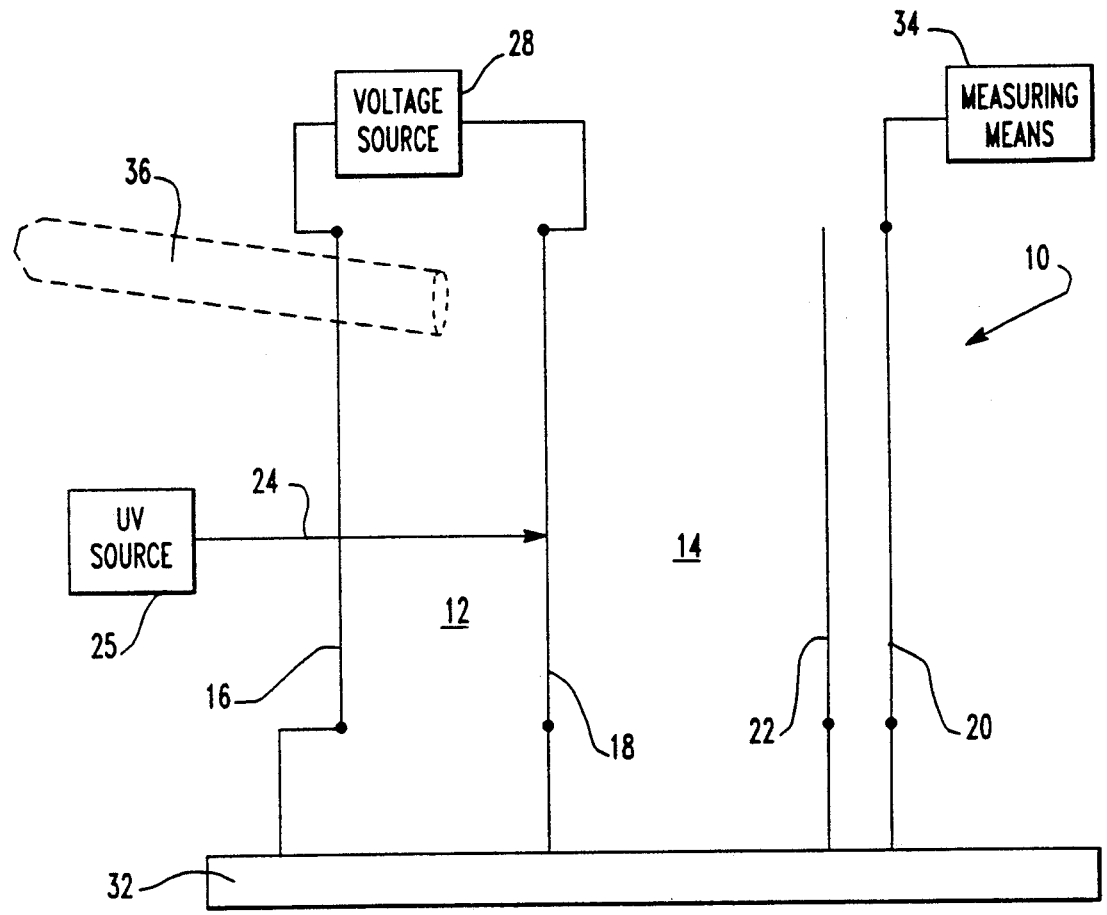
FIG. 1 is a diagrammatic representation of the electrode arrangement of the preferred ion mobility sensor for positive ion sampling.

Referring first to FIG. 1, an ion mobility sensor 10 has two connected regions: an ionization region 12 and a drift region 14. FIG. 1 shows a preferred electrode arrangement which defines the two regions 12, 14 of the sensor 10. The ionization region 12 is bounded by an electrode 16 and a meshed electrode 18. The manner in which the gaseous sample enters the ionization region 12 depends upon whether the sensor 10 is embodied as an open system or as a closed system. If the sensor 10 is embodied as an open system, the area between the grid electrode 18 and the electrode 16 is unconfined and the ambient gas may freely enter the ionization region 12. If the sensor 10 is embodied as a closed system, the sensor 10 would have walls confining the area between the electrode 18 and the electrode 16. Thus, in a closed system, ambient gas is not free to enter the ionization region 12. Any gaseous sample that is to be analyzed must be entered into the ionization region by a feed pipe 36 (shown in dotted line in FIG. 1).

The gaseous sample is entered into the ionization region 12 between the electrode 16 and the electrode 18. The electrode grid 18 separates the ionization region 12 from the drift region 14, and thus also bounds one end of the drift region 14. A shielded collector electrode 20 bounds the end of the drift region 14 opposite to the electrode 18. Although it need not be, the drift region 14 is preferably bounded by walls so as to prevent the entrance or exit of ions from the drift region 14. A meshed shield electrode 22 is preferably located adjacent to the collector electrode 20 and lies between the collector electrode 20 and the electrode 18.

Figure 2:
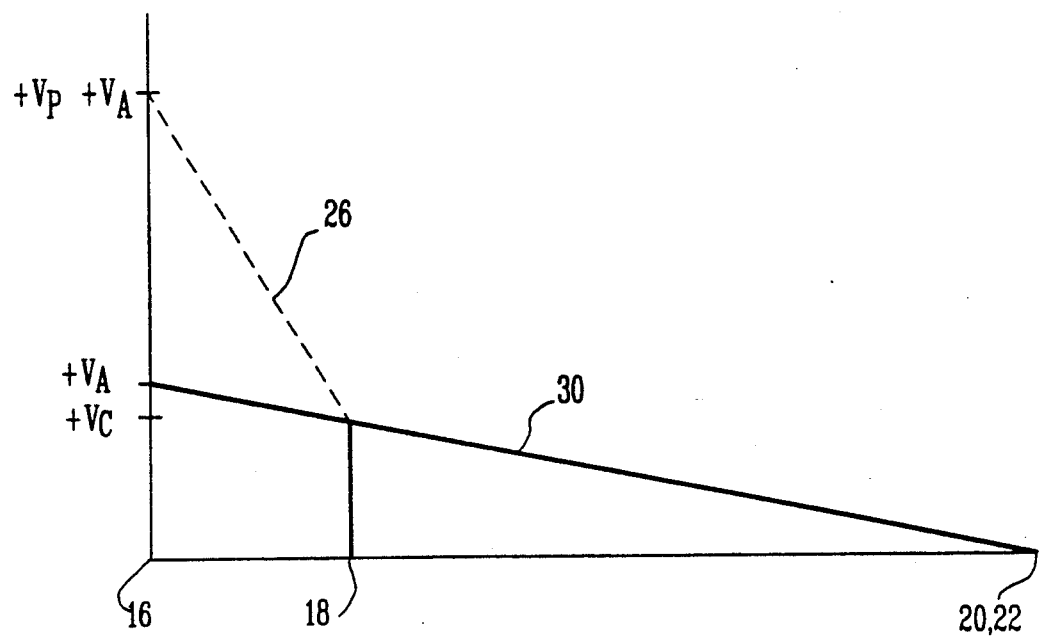
FIG. 2 is a diagrammatic representation of the potential distribution of the preferred ion mobility sensor.

Application of suitable potentials to this electrode arrangement establishes electric fields across the sensor 10. For positive ion sampling, DC voltage potentials 30, as depicted in FIG. 2, are applied by a potential source 32 at the anode 16, the cathode 18 and the shielded collector electrodes 20, 22. Thus, the anode 16 has a voltage of $V_a$, the cathode 18 has a voltage of $V_c$ and the ion collector components (the collector electrode 20 and the shield 22) have a voltage of $V_{ic}$ due to the potential source 30. The applied voltage potentials 30 result in a unidirectional DC drift field $E_d$ across the sensor 10. The drift field $E_d$ is capable of carrying ions from the ionization region 12 through the drift region 14 to the collector electrode 20. In general, the drift time of the different ion species is dependent upon the charge and mass of the particular ions produced in the ionization region. The magnitude of the field $E_d$ is low enough so as not to produce ions in the drift region as a result of electron molecule collisions.

A voltage pulse 26 (depicted as a dotted line in FIG. 2) from an impulse generator 28 is superimposed upon the drift voltage 30 at the anode 16. The superimposed high voltage pulse 26 results in a total anode voltage designated as of $V_a+V_p$ in FIG. 2. The increased voltage applied at the anode 16 results in a field $E_i$ in the ionization region 12 between the anode 16 and the cathode 18. The magnitude of the voltage pulse 26 is selectable, but is chosen so that the generated field $E_i$ is higher in magnitude than the ionizing DC breakdown field of the sample but is also of sufficiently low amplitude and duration so as to avoid the development of an arc in this region. The application of the pulsed voltage 26 results in the potential of the anode 16 being equal to the DC potential 30 at the anode 16 plus the voltage pulse 26.

During the application of the voltage pulse 26, a pulse 24 of ultraviolet (UV) radiation from a suitable UV source 25, such as a flashtube, irradiates the cathode grid 18. The intensity of the UV pulse is selectable and defines the number of photoelectrons released from the cathode of the ionization region 12. Preferably, the anode 16 is of a type that is semi-transparent to UV light, such as a semi-transparent conducting film anode or preferably a grid anode. When the anode 16 is semi-transparent, the UV light pulse 24 may be irradiated through the anode 16 towards the cathode grid 18. By irradiating through the anode 16, the UV source 25 may be located outside of the ionization region 12 while still directing the UV pulse 24 upon the face of the cathode 18.

When the UV pulse 24 reaches the cathode grid 18, the UV light 24 liberates a pulse of photoelectrons from the cathode 18. The greater the intensity of the UV pulse, the larger the number of electrons liberated. The electrons then drift toward the anode 16 creating an avalanche of electron generation. The voltage pulse 26 raises the mean energy of the electrons liberated from the cathode 18 above the ionization level and creates a nonequilibrium discharge situation. With a nonequilibrium discharge, the electrons are at much higher energy than are the heavier particles, i.e., the ions and the neutral particles, resulting in ionization.

Since the disclosed ion mobility sensor 10 provides a pulsed source of ions, a shutter is not needed. While the electrons travel towards the anode 16, the positive ions move towards the cathode grid 18. Because the cathode 18 is a grid, there are gaps between the solid portions of the grid. Those ions which arrive at a solid part of the cathode 18 will get collected. Those ions that arrive at a gap in the cathode grid 18 will be carried through the gap due to the drift field $E_d$. At the time in which the positive ions arrive at the cathode 18, the voltage pulse 26 is off and the steady DC drift field $E_d$ carries the ions.

Because the anode 16, cathode 18, and shield 22 are preferably grids, the UV pulse 24 irradiates the anode 16, cathode 18, shield 22 and collector electrode 20. Any photoelectrons emitted from the anode 16 are prevented from leaving the anode by the applied field $E_i$. However, photoelectrons emitted from the shield 22 and collector electrode 20 begin to drift in the applied drift field $E_d$ towards the cathode 18. In applications in which there are no electronegative species present, these electrons (because of their large drift velocity) arrive at the cathode 18 during the voltage pulse 26 and thereby augment the photoemission from the cathode 18. In applications (such as air) in which there is a large electronegative constituent, electrons emitted from the shield 22 and the collector electrode 20 become attached to form negative ions after drifting a very small fraction of the drift region because of the large three-body attachment coefficient in oxygen at the low applied drift field $E_d$. In this case, any negative charge reaching the ionization region 12 that originates from the shield 22 and collector electrode 20, does so a substantial time after the duration of the voltage pulse 26. In any event, the negative charge arrives in the form of negative ions and therefore, cannot give rise to spurious ionization pulses.

An increase in the ionization field $E_i$ increases the mean energy of the electrons and, therefore, increases the amount of ionization. However, such a variation in the electron distribution also varies the ratio of the coefficients of the different ionization species derived either from different parent molecules in a mixture or from the same molecule as a result of different fragment ions. This ability to tailor the ionization probability among the different neutral gas constituents is one of the unique and advantageous features of the disclosed ion mobility sensor 10. Thus, by deliberately varying the field $E_i$ in the ionization region 12, the probability of ionization of ions having different ionization thresholds can be varied. By providing relatively low energy with the voltage pulse 26, those ions that require the least amount of energy to ionize will ionize. By increasing the value of the voltage pulse 26, and therefore increasing the magnitude of the ionization field $E_i$, higher ionization levels of a given molecule will be reached, accessing different ions. This provides a secondary means of ion discrimination in operation of the sensor 10 allowing the ionization of selected ion species from a sample.

In the nonequilibrium discharge situation, the electrons are of much higher energy than are the heavier particles of either the ions that are generated or the background gas. The ions are at thermal energy and their energy is determined by the background temperature. The mean energy of the electrons in the ionization region 12 is determined solely by the ratio of the electric field $E_i$ between the anode 16 and the cathode 18 divided by the total gas density of the ionization region 12. Therefore, the mean energy of the electrons may be adjusted by adjusting the magnitude of the voltage pulse 26 applied to the anode 16. Also, the number of electrons liberated from the cathode 18 is dependent upon the amount of UV light emitted in each pulse 24. The amount of ionization that occurs to the gaseous sample is dependent upon the magnitude of the electric field $E_i$ produced by the voltage pulse 26. Thus, by offering independent control of both the magnitude of the UV pulse and the magnitude of the voltage pulse, the amount and extent of ionization may be effectively controlled.

The shield 22 is preferably a meshed or grid plate that has a potential associated with it that will keep the drift field $E_d$ uniform. The collector electrode 20 operates at near ground potential preserving the uniformity of the drift field $E_d$. The shield 22 protects the collector electrode 20 from detecting the motion of any induced charge which would otherwise appear on the collector electrode 20. Otherwise, the collector electrode 20 would detect a constant current which would then decrease in steps, where each step would correspond to the collection of a particular species of ion.

Thus, the shield 22 effectively differentiates the current so that no signal is detected at the collector electrode 20 charge passes through the shield 22. Thus, the collector electrode 20 detects a series of electrical pulses in which each pulse is the current due to a given species of ion. Therefore, provided that the mobilities of the different species are known, the pulses collected at the collector electrode 20 provide a signature of the different species present in the sample gas.

Connected to the collector electrode 20 is a means 34 for detecting and measuring the current generated by the ions reaching the collector electrode. Such means are well known in the art and typically involve connecting a transimpedance amplifier to the collector electrode. The transimpedance amplifier converts the incoming ion charge to a voltage signal.

Although the electrodes of the preferred ion mobility sensor are configured to collect positive ions, it is understood the polarity of the electrodes could be reversed for the collection of negative ions.

Figure 3:
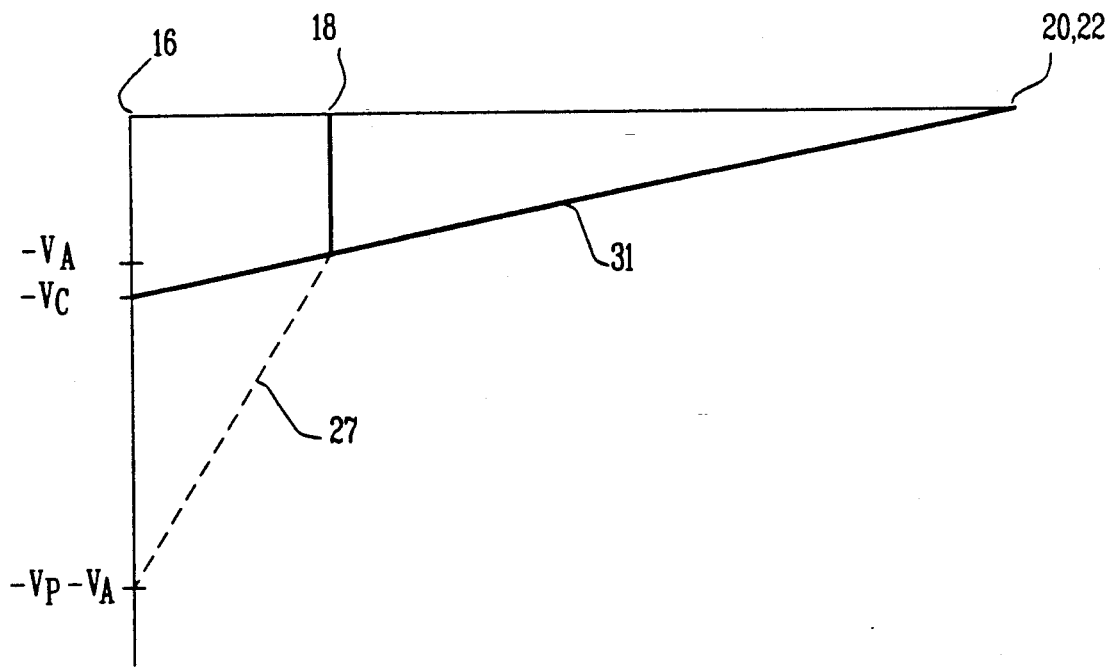
FIG. 3 is a diagrammatic representation of the potential distribution of the preferred ion mobility sensor for negative ion sampling.

For negative ion collection, the potential distribution is as shown in FIG. 3 where now electrode 16 becomes the cathode and electrode 18 becomes the anode of the ionization region 12. Application of negative polarity potentials 31, as depicted in FIG. 3, from source 32 result in a voltage of $-V_a$ at the anode 18, and $-V_c$ at the cathode 16, and ensure a unidirectional DC electric field across the sensor. A negative polarity voltage pulse 27 (depicted as a dotted line in FIG. 3) from generator 28 is superimposed on the voltage of electrode 16 and results in a total cathode voltage designated at $-V_c-V_p$ in FIG. 3. The photoelectron pulse released from the cathode 16 as a result of irradiation by the UV pulse during the application of the voltage pulse 27 triggers a non-equilibrium discharge between electrodes 16 and 18 which define the ionization region. Negative ions formed in the ionization region then drift towards electrode 18 and a fraction of them continue to drift through the meshed anode 18 under the influence of the DC drift field and enter the drift region. Once in the drift region the negative ions continue to drift toward the collector and are eventually sampled in a similar way to that described earlier for positive ions. The establishment of a non-equilibrium discharge in the ionization region ensures the production of negative ions formed by the dissociative attachment process as well as by electron capture by the parent molecule.

Figure 4:
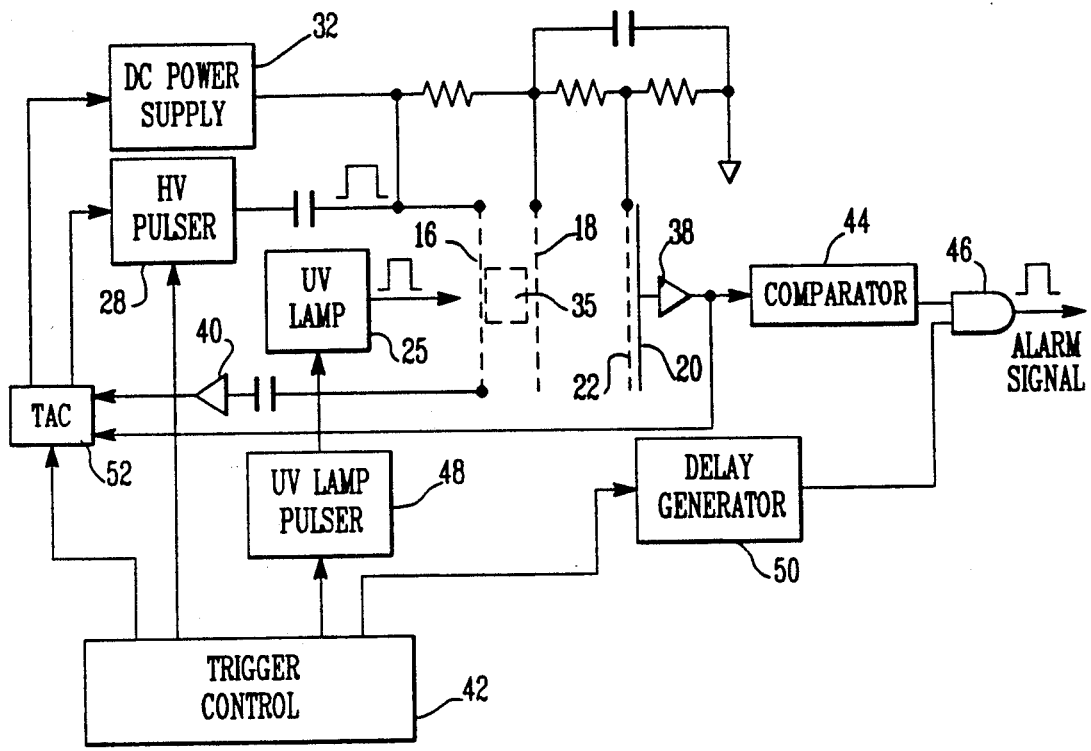
FIG. 4 is a diagrammatic representation of the alarm circuitry for the first preferred implementation of the ion mobility sensor.

Referring next to FIG. 4, a diagrammatic representation of an ion mobility sensor is shown in which a first preferred implementation, an alarm system, is employed. The electrodes are configured for the case where a single positive ion species is monitored in an electronegative sample, although as already noted the polarity of the electrodes could be reversed for monitoring negative ion species. A positive DC voltage is applied to the electrodes 16, 18, 20 and 22 with the appropriate potentials for providing a unidirectional, approximately uniform electrical field from the anode 16 to the collector electrode 20. The value of the electric field in the drift area $E_d$ is such as to ensure that between the anode 16 and the collector electrode 20 the ions are in thermal equilibrium with the sample gas. A capacitor connected across the drift region is used to maintain a constant field $E_d$ in the region.

A voltage pulse 26 is capacitively coupled to the anode 16 from a high voltage pulser 28 such as a pulse transformer, triggered from the trigger controller 42. The amplitude of the voltage pulse 26 is sufficiently high so that the ratio of the total electrical field between the anode 16 and the cathode 18 to the total sample gas density N is above the ionization threshold value for the particular sample under investigation. Both the DC and pulse amplitudes are variable.

Figure 5:
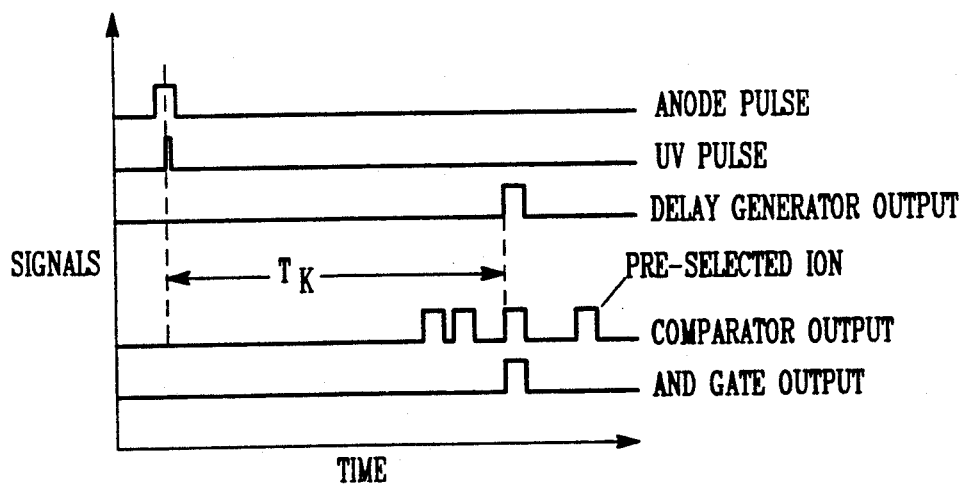
FIG. 5 is a diagrammatic representation of the alarm signal timing for the first preferred implementation of the ion mobility sensor.

A UV lamp pulser 48 is triggered by a pulse from the trigger controller 42 and provides the drive power for the UV light source 25 which may, for example, be a xenon flashtube equipped with a UV transmitting window. The resulting UV pulse is arranged to be delayed with respect to the anode voltage pulse and contained within the anode pulse envelope duration as indicated in the timing diagram of FIG. 5. The incidence of the resulting UV pulse at the cathode 18 gives rise to a pulsed discharge which is self-quenched on decay of the voltage pulse 26. The relative position of the UV pulse 24 with respect to the voltage pulse 26, together with the amplitude and width of the voltage pulse 26 are adjusted for optimum ion discharge intensity for a predetermined sensitivity within the limitation that the discharge not develop into an arc.

The electrodes are coupled to a first and a second transimpedance amplifiers 38, 40. The first transimpedance amplifier 38 is coupled to the collector electrode 20 for positive ion species measurement.

The output from the first transimpedance amplifier 38 is fed to a comparator set 44 to provide a standard logic pulse when the detected signal is above a preset level. Thus, the output from the comparator 44 consists of a sequence of logic pulses corresponding to the arrival of pulses of different positive ion species at the collector electrode 20 when the amplitudes of these pulses are above the preset level. The output from the comparator 44 is then connected to one input of an AND gate 46. The other input of the AND gate 46 is connected to a delay generator 50 which outputs a logic pulse at a predetermined time following the UV pulse trigger 48. This predetermined time corresponds to the known transit time of the monitored ion species. Thus, if both pulses are coincident at the AND gate 46 an output is derived from the AND gate 46 which may be used to trigger an appropriate alarm 54.

Figures 6, 7:
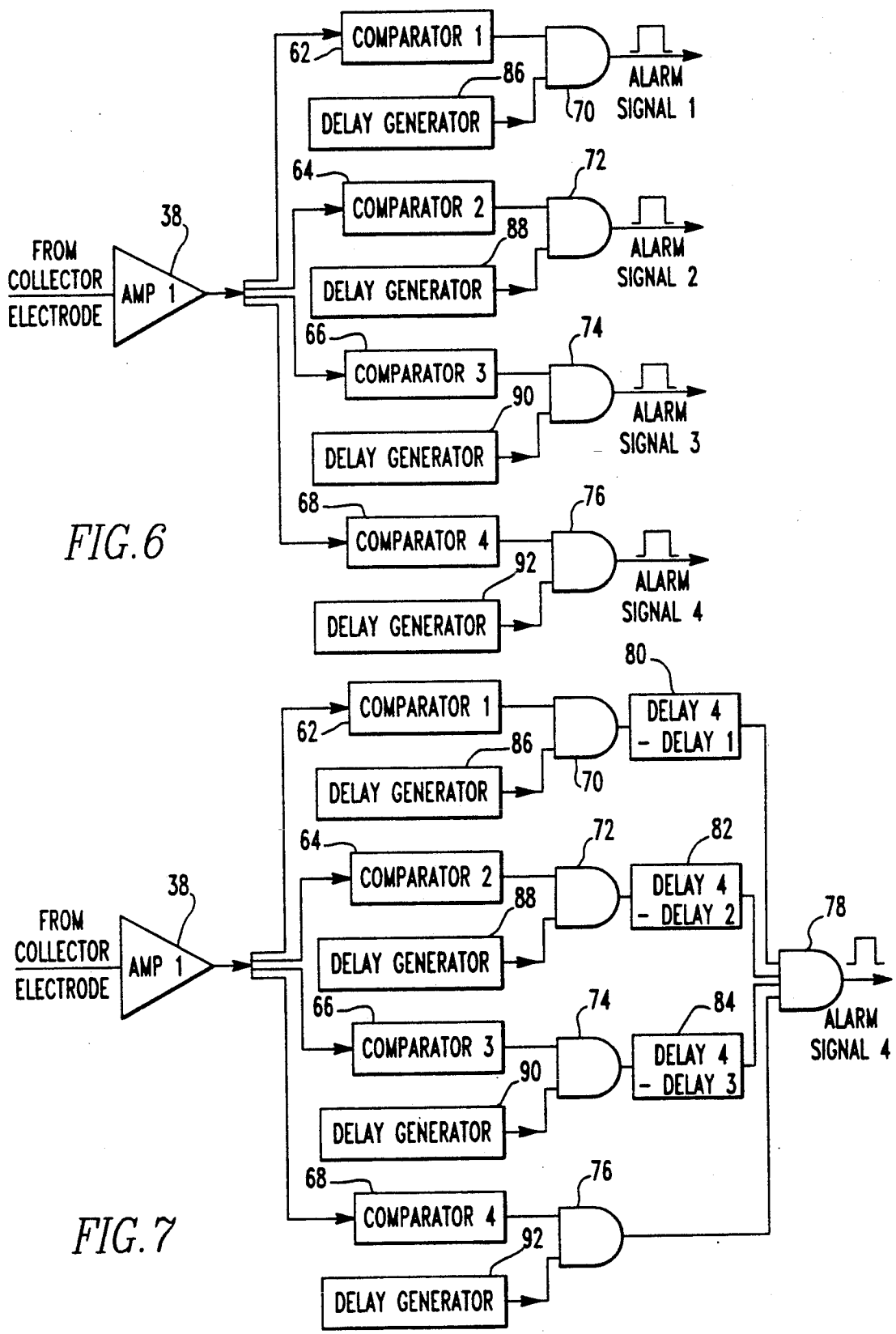
FIG. 6 is a diagrammatic representation of the alarm circuitry for an alternative to the first preferred implementation of the ion mobility sensor.
FIG. 7 is a diagrammatic representation of the alarm circuitry of another alternative to the first preferred implementation of the ion mobility sensor.

A variation of the first preferred implementation of the ion mobility sensor is shown in FIG. 6. In this variation, the simultaneous monitoring of n multiple ion species is accomplished where the different species trigger alarms when the levels of these species rise above different preset levels. An example of this system for the case of n=4 is shown in FIG. 6. The output from the first transimpedance amplifier 38 is directed to four different comparators 62, 64, 66 and 68 in which the individual alarm limit levels are set. Each comparator 62, 64, 66, 68 feeds an input of a respective AND gate 70, 72, 74, 76. Delay generators 86, 88, 90, 92 feed the other input of the respective AND gates 70, 72, 74, 76. The delay generators 86, 88, 90, 92 may be part of one delay generator unit or may be separate units similar to the delay generator 50 of FIG. 4. Each AND gate is set to emit an alarm pulse at the coincident arrival of pulses from the comparators and appropriately delayed pulses from the delay generator corresponding to the specific transit times of the different ion species. One of the channels shown in FIG. 6 may alternatively be used to provide a test signal by detecting an ion characteristic of the majority sample and which should always be present regardless of minority impurities.

Another variation of the first implementation is the alarm system shown in FIG. 7. In this alternative, the alarm signal is output only if, for example, a number of different ion species (four species being demonstrated in FIG. 7) derived from the same or related impurity molecules are detected. In this arrangement, the outputs from the individual AND gates 70, 72, 74, 76 following the comparators 62, 64, 66, 68 and delay generators 86, 88, 90, 92, respectively, are fed after suitable delay to a multi-input AND gate 78. These delays 80, 82, 84 are added to all but a reference species and are such so as to compensate for the different known transit times of specific ion species so that all input signals to the multi-input AND gate 78 arrive simultaneously. This may be accomplished by adding a delay to the signals of the species equal to the delay of a reference species minus that species' delay. For example, if the species preset at comparator 68 is the reference and has a delay (transit time) of $t_4$, the species of comparator 62 which has a delay of $t_1$, has a delay added to it equal to $t_4 - t_1$ (shown as 80 in FIG. 7). When this delay is added to $t_1$, the total delay for the species of comparator 62 is $t_1 + (t_4 - t_1)$ which is $t_4$. This step would also be performed on the species of comparators 64 and 66. Thus, for the case in which the species of comparator 68 is the reference, all species will be delayed by the same time, $t_4$. It is preferable for the species having the longest transit time to be chosen as the reference. When all four input signals to the multi-input AND gate 78 arrive simultaneously, an output alarm pulse is triggered. This system would be incorporated to reduce the occurrence of false alarms due to possible interference from unrelated species.

In the alternative shown in FIG. 7, the control of the sensor may either be local, such as by toggling a switch, or remote. In the latter case, the control signal can be carried by conventional cable, fiber optic cable, RF telemetry or any convenient means depending on the particular nature of the sensor environment. It is distinctly understood that although four comparators for four different species have been discussed in the alternatives of FIGS. 6 and 7, the number of comparators utilized, and the number of species monitored is not limited to four but may be any number.

Figure 8:
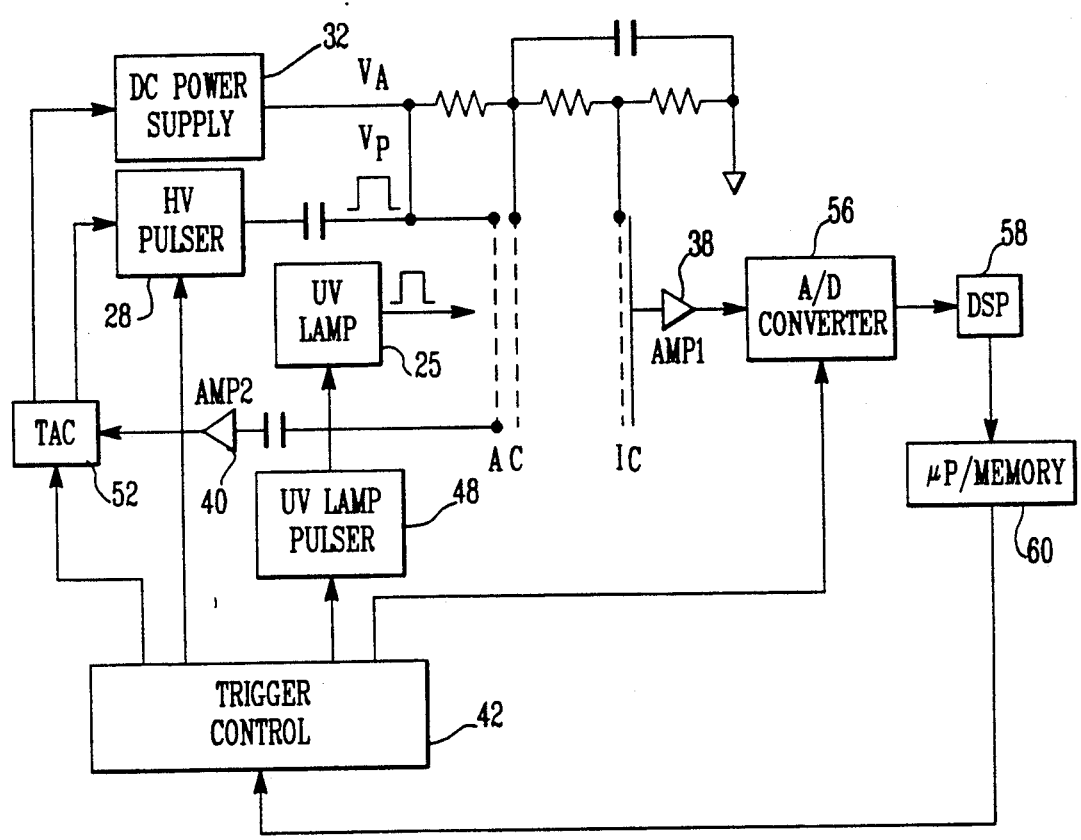
FIG. 8 is a diagrammatic representation of the circuitry for a second preferred implementation of the ion mobility sensor.

A second preferred implementation is shown in FIG. 8. This embodiment integrates the sensor into a quantitative microprocessor-based system for the comprehensive measurement of one or more different programmable species. The electronic arrangement for this embodiment is similar to that of the embodiment shown in FIG. 4 except that the comparator and AND gate have been replaced by an analog-to-digital converter (A/D converter) 56 and some kind of microprocessor 58.

In addition to triggering the ionization, the trigger control 42 triggers the A/D converter 56 to start accepting data. The A/D converter 56 then receives the output voltage from the first transimpedance amplifier 38 and digitizes it. The digitized signal is then processed in the digital signal processor 58. The signal processing could involve providing look up tables in memory 60 that represent various ion species. The digitized signals derived from the collected ions would then be compared to the look up table values. This comparison would allow determination of which species were present in a sample and in what amounts.

It is preferred that the voltage pulser and the UV pulse source may operate to repetitively pulse the voltage and UV light pulses. It is also preferred that the digital signal processor and memory unit cooperate to store the digital output from the analog to digital converter and provide signal averaging of the ion signals and thereby improve the signal/noise ratio.

In order to maintain calibrated operation of the sensor, it is necessary to monitor the total gas density N in the sensor, since variations in N lead to corresponding variations in the ratios $E_i/N$ and $E_d/N$. The circuit of FIG. 4 includes the means to automatically compensate the magnitudes of the DC positive or negative drift voltages 30 or 31 and the positive or negative voltage pulses 26 or 27 so as to maintain the ratios $E_i/N$ and $E_d/N$ at their preset reference values. The ion drift velocity $w_k$ is related to the reduced ion mobility $\mu_{k0}$ through the expression $w_k = \mu_k E_d = \mu_{k0} (E_d/N) N_0$, where $N_0 (=2.688 \times 10^{19} \text{cm}^{-3})$ is the gas number density corresponding to 760 Torr at 273° K. Substituting the equation $t_k = d_d/w_k$ into the above expression yields the relation $N = (\mu_{k0} E_d N_0/d_d) t_k$. Since the quantity $\mu_0 E_d N_0/d_d$ is constant for a fixed drift field $E_d$, the total density N is proportional to the ion transit time $t_k$. Thus, if the transit time of an ion species derived from one of the sample constituents which is always present, such as oxygen for the case in which air is the sample, is monitored, a measure of the total gas density may be obtained. Any positive or negative ion may be selected for this purpose since all are in thermal equilibrium with the sample. In the configuration of FIG. 4 in which a negative ion is being monitored for density compensation, it is the output from the second transimpedance amplifier 40 (which is connected to the anode 16) that provides the feedback.

Figure 9:
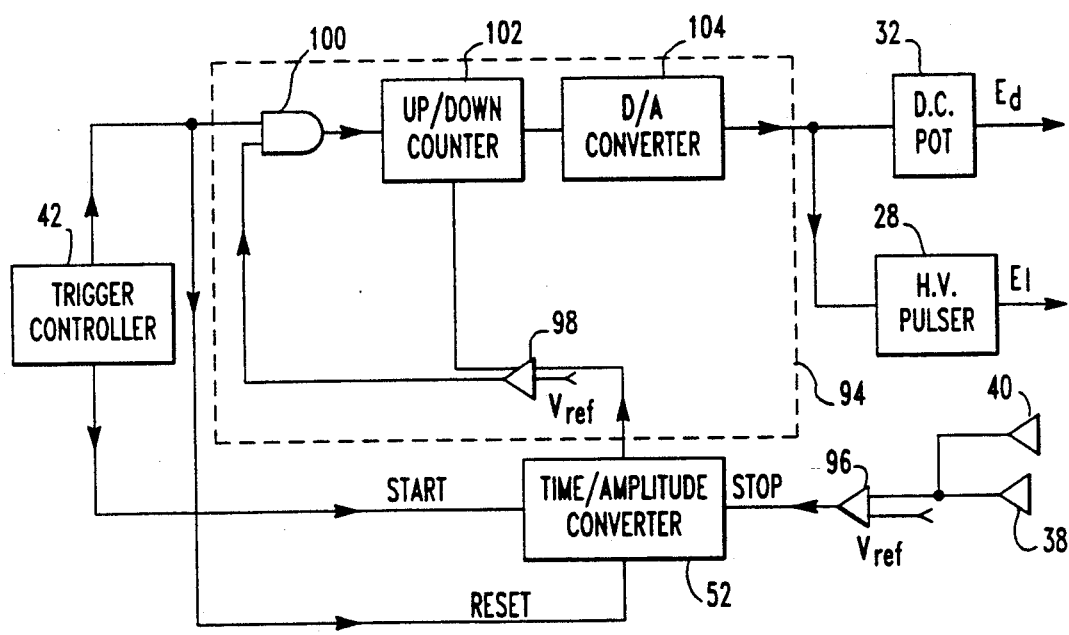
FIG. 9 is a diagrammatic representation of a feedback control circuit that may be used in the automatic compensation system.

Referring to FIGS. 4 and 9, the trigger control 42 sends an initial signal to the time to amplitude converter 52 while simultaneously activating the transmission of the UV pulse and the voltage pulse. The output from the second transimpedance amplifier 40 is sent to the time to amplitude converter 52 which derives a voltage signal. Preferably the output from the second transimpedance amplifier is first directed through a comparator 96. The comparator 96 which also has a reference voltage input to it, outputs a logic pulse. The time to amplitude converter output voltage is proportional to the time delay between the initial trigger control signal and the arrival time of the negative ion pulse (formed in the close proximity of the collector electrode 20) at the anode 16 which represents the negative ion drift time from the collector electrode 20 to the anode 16. This voltage signal, which is proportional to the total density N, is then used in a feedback controller circuit to adjust the drift voltage potentials 30 and/or the voltage pulse 26. Such feedback correction circuits are well known and the feedback control circuit 94 shown in FIG. 9 is provided as an example, it being understood that any feedback control circuit may be used. In the feedback control circuit 94 of FIG. 9, the voltage signal from the time to amplitude converter is fed to an error amplifier 98. A reference voltage is also input to the amplifier 98 which represents the drift time of the selected ion species at standard conditions. The time to amplitude converter output is compared to the reference voltage and a signal is generated by the amplifier 98 when the difference in the voltages is above some preset amount. The signal generated by the amplifier 98 is fed to one input of an AND gate 100 and a delayed signal from the trigger controller 42 is fed to the other input of the AND gate 100. When both signals are coincident at the AND gate 100, the counter 102 is indexed by one digital unit. The amplifier 98 further provides either a positive or negative sign to the counter digital output. The digital output is then converted to an analog signal in the digital to analog converter 104. This analog signal biases the DC potential source and the voltage pulser to adjusted outputs.

Thus, as the total density changes due to changes in temperature and pressure, the fields $E_i$ and $E_d$ change proportionally to the density change. In this way, both $E_i/N$ and $E_d/N$ may be automatically held constant which, in turn provides normalization of the sensitivity and ion transit timing, respectively. Alternatively, the voltage signal from the time to amplitude converter 52 may be used to interpolate the appropriate correction to the drift potentials 30 and voltage pulses 26 via stored look-up tables. This normalization system may be provided in any ion mobility sensor regardless of electrode configuration and ionization technique.

Alternatively, in the electrode configuration of FIG. 4, a positive ion species may be utilized for automatic density feedback control by coupling a first transimpedance amplifier 38 to the collector electrode 20. The output from the first transimpedance amplifier 38 then additionally drives the time to amplitude converter 52 which derives a voltage signal proportional to the time delay between the UV light pulse 24 and the arrival time of the selected positive ion pulse (formed in the ionization region 12) at the collector electrode 20. This signal is then utilized as described above for the negative ion case to derive a voltage adjustment.

Additionally, the automatic compensation system described above may be utilized in an electrode configuration in which the polarity of the voltage potentials is reversed so that electrode 16 is a cathode and electrode 18 an anode. In this electrode configuration, the first transimpedance amplifier 38 would receive charges from the negative ion species collected at the collector electrode 20 and a species that is always present is selected to monitor the density.

It is understood that the above-described compensation system is not limited to the preferred ion mobility sensor but may be utilized in any ion mobility sensor that has an ionization region and a collector electrode. In the case in which an ion mobility sensor utilizes a voltage pulse ionization, the compensation system may adjust the drift field and the ionization field. In cases in which a pulsed ionization is not employed, the compensation may be used to adjust the drift field only. Ion mobility sensors are known that do not employ pulsed ionization means and instead utilize a continuous ionizing source such as a continuous radiation source 35 shown in dotted line in FIGS. 4 and 8. Ni-63 is a preferred radiation source for this purpose. Continuously ionizing sensors typically use a shutter electrode which may be electrode 18 in FIGS. 4 and 8 to inject the ions into the drift region in pulses. In this type of sensor, the shutter pulse may be utilized to provide the initial signal to the time to amplitude converter. The remainder of the adjustment system would operate substantially identically as in the pulsed ionization case described above. Thus, regardless of the type of ionization means chosen or of the electrode configuration, changes in the temperature and pressure within an ion mobility sensor may be automatically compensated for by monitoring the actual travel time of an ion species and comparing it to the travel time of that species at known pressure and temperature.

While a present preferred embodiment of the invention has been shown, it is distinctly understood that the invention is not limited thereto but may be otherwise variously embodied within the scope of the following claims.

I claim:

1. A system for compensating for changes in pressure and temperature in an ion mobility sensor, the sensor having an ionization region being connected to a drift region, the sensor comprising:
    (a) a boundary grid electrode providing a boundary between the ionization region and the drift region;
    (b) a second electrode provided at an end of the drift region opposite to the boundary electrode, wherein a voltage potential is applied to the electrodes creating a unidirectional electric field between the electrodes;

(c) an ionization source located in the ionization region proximate the boundary electrode for generating ions in the sensor;

(d) a trigger controller connected to at least one of the boundary electrode and the ionization source for allowing ions to enter the drift region proximate to the boundary electrode at a time $t_1$;

(e) means connected to the second electrode for measuring a time $t_2$ at which a selected ion species travels from the boundary electrode to the second electrode;

(f) a time to amplitude converter for generating a voltage signal proportional to a difference between $t_1$ and $t_2$, the voltage signal representing the actual travel time of the selected ion species from the boundary electrode to the second electrode; and (g) a feedback control circuit connected to the time to amplitude converter for adjusting the electrode voltage potential by an amount proportional to a difference between the actual travel time voltage and a voltage proportional to the reference travel time of the selected ion species between the boundary and second electrodes at a known pressure and temperature.

2. The system of claim 1 wherein the ionization source is a continuous ionization source located in the ionization region proximate the boundary electrode, and wherein the boundary electrode is shutter electrode that is activated by a voltage applied to it from the trigger controller.

3. The system of claim 2 wherein the feedback control circuit further adjusts the voltage applied to the shutter electrode.

4. The system of claim 2 wherein the continuous ionization source is Ni-63.

5. The system of claim 2 wherein the means for measuring $t_2$ is a transimpedance amplifier connected to the second electrode for converting the ion charge received at the second electrode into a voltage signal that is directed to the time to amplitude converter.

6. The system of claim 1 further comprising a first electrode positioned at an end of the ionization region opposite to the boundary electrode, wherein the voltage potential is also applied to the first electrode so that the unidirectional field is created between all the electrodes, and wherein the ionization source is a pulsed voltage applied to the first electrode and a pulse of UV light applied to one of the first electrode and the boundary electrode, and wherein the voltage and UV pulses are activated by the trigger controller.

7. The system of claim 6 wherein the feedback control circuit further adjusts the voltage pulse applied to the first electrode.

8. The system of claim 6 wherein ions are formed at the boundary and second electrodes by the ionization source.

9. The system of claim 8 wherein the means for measuring $t_2$ is at least one transimpedance amplifier connected respectively to at least one of the first and second electrodes for converting the ion charge received at the at least one of the first and second electrodes into a voltage signal that is directed to the time to amplitude converter.

10. The system of claim 6 wherein the polarity of the potentials applied to the electrodes causes electronegative ions to be collected at the second electrode, and wherein the UV light pulse is applied to the first electrode.

11. The system of claim 6 wherein the polarity of the potentials applied to the electrodes causes electropositive ions to be collected at the second electrode, and wherein the UV light pulse is applied to the boundary electrode.

12. A method of compensating for changes in pressure and temperature in an ion mobility sensor, the sensor having an ionization region being connected to a drift region, the sensor comprising the steps of:

(a) providing a boundary electrode that defines a boundary between the ionization region and the drift region;

(b) providing a second electrode at an end of the drift region opposite to the boundary electrode, wherein a voltage potential is applied to the electrodes creating a unidirectional electric field between the electrodes;

(c) creating ions of a gaseous sample proximate the boundary electrode;

(d) directing the ions into the drift region proximate the boundary electrode at a time $t_1$;

(e) measuring a time $t_2$ at which a selected ion species travels form the boundary electrode to the second electrode;

(f) generating a voltage signal proportional to a difference between $t_1$ and $t_2$, the voltage signal representing the actual travel time of the selected ion species from the boundary electrode to the second electrode; and (g) adjusting the electrode voltage potential by an amount proportional to a difference between the actual travel time voltage and a voltage proportional to the reference travel time of the selected ion species between the boundary and second electrodes at a known pressure and temperature.

13. The method of claim 12 wherein the ions are created by a continuous ionization source positioned within the ionization region proximate to the boundary electrode and wherein the boundary electrode is a shutter electrode being activated by a shutter voltage.

14. The method of claim 13 wherein the shutter voltage is adjusted by the amount proportional to the difference between the actual travel time voltage and the voltage proportional to the reference travel time of the selected ion species.

15. The method of claim 13 wherein $t_2$ is measured by a transimpedance amplifier connected to the second electrode for converting the ion charge received at the second electrode into a voltage signal.

16. The method of claim 15 wherein the voltage signal proportional to the difference between $t_1$ and $t_2$ representing the actual travel time of the selected ion species is derived in a time amplitude converter which receives voltage signals representing $t_1$, from a trigger controller as the trigger controller activates the shutter, and voltage signals representing $t_2$ from the transimpedance amplifier.

17. The method of claim 12 further comprising providing a first electrode positioned at an end of the ionization region opposite to the boundary electrode, wherein the voltage potential is also applied to the first electrode so that the unidirectional field is created between all the electrodes, and wherein the ions are created by a pulsed voltage applied to the first electrode and a pulse of UV light applied to one of the first electrode and the boundary electrode.

18. The method of claim 17 wherein the voltage pulse and UV pulses are activated by a trigger controller.

19. The method of claim 17 wherein the UV light pulse is applied to the first electrode and wherein the potentials applied to the electrodes causes electronegative ions to be collected at the second electrode.

20. The method of claim 17 wherein the UV light pulse is applied to the boundary electrode and wherein the potentials applied to the electrodes causes electropositive ions to be collected at the second electrode.

* * * * *